United States Patent
Ahlmen et al.

(10) Patent No.: US 7,347,207 B2
(45) Date of Patent: Mar. 25, 2008

(54) ANESTHESIA APPARATUS WITH REMOTE CONTROL DURING OPERATION IN A MANUAL VENTILATION MODE

(75) Inventors: Christer Ahlmen, Sollentuna (SE); Mario Loncar, Ekerö (SE); Petter Videbrink, Upplands Väsby (SE)

(73) Assignee: Maquet Critical Care AB, Solna (SE)

( * ) Notice: Subject to any disclaimer, the term of this patent is extended or adjusted under 35 U.S.C. 154(b) by 0 days.

(21) Appl. No.: 10/701,333

(22) Filed: Nov. 4, 2003

(65) Prior Publication Data
US 2004/0099267 A1 May 27, 2004

(30) Foreign Application Priority Data
Nov. 20, 2002 (SE) .................................... 0203430

(51) Int. Cl.
*A61M 11/00* (2006.01)
(52) U.S. Cl. ............................ 128/204.28; 128/204.18; 128/204.21
(58) Field of Classification Search ........... 128/203.12, 128/203.13, 203.28, 204.18, 204.21, 204.23, 128/204.28, 205.13, 205.14, 205.17, 205.23
See application file for complete search history.

(56) References Cited

U.S. PATENT DOCUMENTS

| | | | |
|---|---|---|---|
| 5,231,981 A | 8/1993 | Schreiber et al. | |
| 6,240,921 B1 | 6/2001 | Brydon et al. | |
| 6,415,792 B1 | 7/2002 | Schoolman | |
| 6,834,647 B2 * | 12/2004 | Blair et al. | 128/204.18 |
| 2001/0035186 A1 | 11/2001 | Hill | |
| 2002/0017299 A1 | 2/2002 | Hickle | |

FOREIGN PATENT DOCUMENTS

| | | |
|---|---|---|
| EP | 1 178 288 | 2/2002 |
| EP | 1 287 843 | 3/2003 |
| WO | WO 95/28193 | 10/1995 |
| WO | WO 99/62403 | 12/1999 |

* cited by examiner

*Primary Examiner*—Steven O. Douglas
(74) *Attorney, Agent, or Firm*—Schiff Hardin LLP

(57) ABSTRACT

An anaesthetic device has a manual ventilation bag, a mechanical ventilator and a user interface for setting an operating mode, including mechanical ventilation via the mechanical ventilator and manual ventilation via the manual ventilation bag, and for setting parameter values for the operating mode that has been set. The anaesthetic device further has a remote control for wireless transmission of commands to the user interface. The user interface is adapted to carry out the commands from the remote control only when the anaesthetic device is set for manual ventilation.

8 Claims, 1 Drawing Sheet

ANESTHESIA APPARATUS WITH REMOTE CONTROL DURING OPERATION IN A MANUAL VENTILATION MODE

BACKGROUND OF THE INVENTION

1. Field of the Invention

The present invention relates to an anaesthesia apparatus of the type having a manual ventilation bag, a mechanical ventilator, and a user interface for selecting an operating mode of the apparatus.

2. Description of the Prior Art

Anaesthesia apparatuses generally are designed to operate in many different operating modes. Two of these are manual ventilation, in which the anaesthetist controls/supports the breathing of a patient by means of a manual ventilation bag, and mechanical ventilation, in which the breathing of the patient is controlled/supported by means of a mechanical ventilator (the mechanical ventilation may itself be divided in to a number of sub-modes such as pressure regulation, volume regulation, etc.).

The set-up of an operating mode generally is done via a user interface (which itself may include several components located at different parts of the anaesthetic device). Parametric values for the different operating modes also may be entered via the user interface.

During manual ventilation the operator usually is located close to the patient and with one hand can control a facemask on the patient and with the other controls the manual ventilation bag. This usually occurs during the course of administering the anaesthetic.

A problem with this conventional technique is that in order to make changes to the entered parameters, the anesthesiologist is forced to divert his or her attention from the patient during the time it takes to make the changes via the user interface.

SUMMARY OF THE INVENTION

An object of the present invention is to provide an anaesthetic device in which the above-described problem is wholly or partially alleviated.

The above object is achieved in accordance with the present invention in an anaesthesia apparatus having a manual ventilation bag, a mechanical ventilator, and a user interface allowing selective setting of an operating mode, including a mechanical ventilation mode using the mechanical ventilator and a manual ventilation mode using the manual ventilation bag, and allowing setting of parameter values for the selected mode, and having a remote control in wireless communication with the user interface for wirelessly transmitting commands to the user interface, the user interface responding to and implementing the commands form the remote control only when a manual ventilation mode has been selected.

With a remote control for the more important functions of manual ventilation the operator is able to maintain undivided attention on the patient while the parameters are being changed by the remote operation of the user interface. The remote control and the user interface are adapted so that the remote control can be used only during manual ventilation. Thus, during mechanical ventilation the remote control cannot affect the installed settings, which means that no unintentional changes can be made during mechanical ventilation.

In this connection, it is an advantage for the remote control to include controls for the regulation of fresh gas flow and permitted over-pressure level, these being the more important machine parameters for manual ventilation. The controls may, to this end, be realized as a wheel (analogous to a computer mouse wheel) but with a distinct position related to a predetermined setting of the parameters. These parameters may be permanently programmed for the device, or may be programmable for every patient, or may be values that are programmed by the operator for use when manual ventilation is switched in. With the last-mentioned alternative, the wheel can be made to automatically occupy this distinct position as soon as manual ventilation is switched in. This may be easily achieved using a control signal from the user interface to the remote control and a small drive motor for the wheel responsive to this signal.

Moreover, the remote control may include push-buttons for oxygen flushing and alarm shut-off. When the above-described wheels are used as the controls they may also be provided with a push-button functionality for the oxygen flushing and the alarm shut-off. In this way the remote control may be made small, lightweight and easy to use.

It is furthermore an advantage for the remote control to be provided with a fastener, for example a hook-and-loop (Velcro®) strip, by which the remote control may be attached to a suitable site during use. The remote control, for example, may be attached to the anesthesiologist's wrist, to the patient's facemask, to the patient, to the manual ventilator, etc.

DESCRIPTION OF THE DRAWINGS

FIG. 2 shows a remote control for the anaesthesia apparatus in accordance with the invention.

DESCRIPTION OF THE PREFERRED EMBODIMENTS

Figure 1:
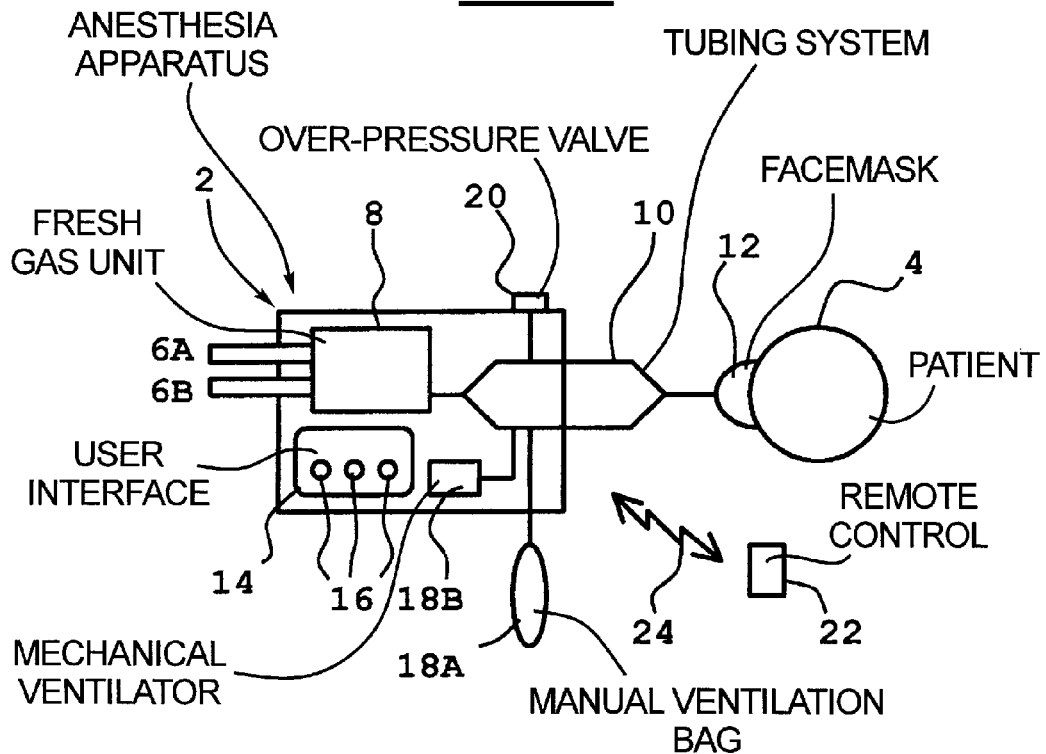
FIG. 1 is a schematic block diagram of an anaesthesia apparatus according to the invention, connected to a patient.

An anaesthesia apparatus 2 according to the invention is shown schematically in FIG. 1. The anaesthetic device is connected to a patient 4 to be anaesthetized.

Some of the components for the preparation of fresh gas in the anaesthesia apparatus 2 are a first gas connection 6A for nitrous oxide; a second gas connection 6B for oxygen; and a fresh gas unit 8 for the blending of a chosen mixture of nitrous oxide and oxygen and possibly even for supply of an anaesthetic agent.

Other arrangements for the preparation of fresh gas are known and the anaesthesia apparatus 2 may equally as well include one or more of these.

The fresh gas is conducted via a tubing system 10 to a facemask 12 that is placed over the mouth and nose of the patient 4. It should be noted that several different tubing systems are used in the field of anaesthesiology, for example an open system without re-breathing; a half-open system such as Bain and Mapelson with partial re-breathing; and a closed system with substantial re-breathing. The anaesthesia apparatus 2 is able to operate with any of the above tubing systems and even with other known tubing systems or combinations of tubing systems.

Similarly, different designs of the facemask 12 are known and even tracheal or tracheotomy tubes may be employed without departing from the invention.

An anesthesiologist may set an operating mode for the anaesthesia apparatus 2 as well as parametric values by means of a user interface 14. The user interface 14 has, in the present example, some form of input units 16. The user interface 14 may be based on physical input units; software based input units (interactive screens) or a combination thereof.

The anaesthesia apparatus 2 is able to operate in both manual and mechanical ventilation modes and is therefore provided with a manual ventilation bag 18A and a mechanical ventilator 18B. The connection of these to the tubing system 10 may be made in many different known ways and so need not be described in detail.

An over-pressure valve 20 is also connected to the tubing system 10. The over-pressure valve 20 opens at a settable over-pressure level and is usually known as an APL-valve.

During manual ventilation of the patient 4 the anaesthesiologist generally needs to closely monitor the patient 4 as well as the manual ventilation bladder 18A. To then make changes to settings (including switching alarms off) using the user interface 14 worsens the working situation of the anesthesiologist, which results in a reduced control over the patient 4.

The anaesthesia apparatus 2 therefore is designed with a remote control 22 for the remote adjustment of at least some functions with manual ventilation. The remote control 22 communicates wirelessly with different parts of the anaesthetic device 2, as is indicated by the arrow 24.

Figure 2:
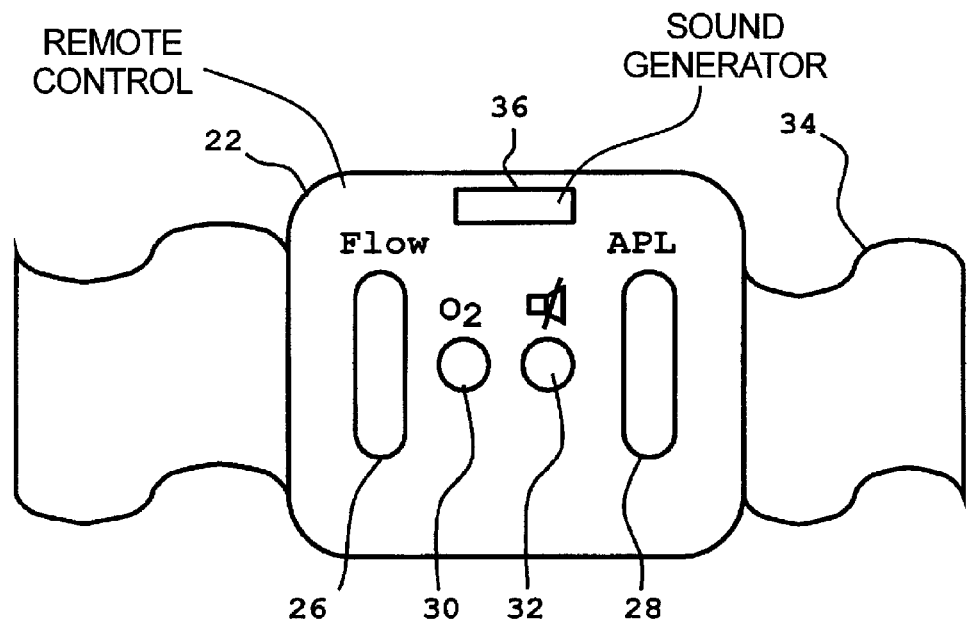
FIG. 2 shows a remote control for the anaesthetic device.

An exemplary embodiment of the remote control 22 is shown in FIG. 2. The remote control 22 has, in this example, a control for setting the fresh gas flow. This assumes that the anaesthetic device has an electronically regulated fresh gas system. The control is devised, as shown in FIG. 2, devised as a first wheel 26, the rotation of which influences the flow setting.

In order to be able to work from some form of reference position it is desirable to provide the first wheel 26 with a distinct position. With only one revolution of the wheel 26 the flow may be increased or decreased dependent on the direction of rotation of the first wheel 26 with respect to this distinct position.

Alternatively, the first wheel 26 may be able to rotate through several revolutions. Each revolution may then be equated to a predetermined change in the flow and by counting the distinct positions the operator is able to determine what change has been made.

The starting point for the control may be the distinct position for the first wheel 26, that corresponds to a device constant for the fresh gas flow. It is preferable, however, for this value to be selected for each patient. It is even possible to adapt the system so that the anesthesiologists, in connection with the selection of manual operating mode, sets-up the fresh gas flow that then constitutes the value for the distinct position.

It is an advantage, in connection with the switching in of manual ventilation on the user interface, for the first wheel 26 to assume the distinct position (regardless of the previous position). This may be easily achieved using a small motor to drive the wheel 26 to this position on receipt of a signal from the user interface indicating that manual ventilation is switched in.

The remote control 22 is provided with a control for setting the allowed over-pressure level. This assumes that the over-pressure valve (APL-valve) is provided with electronic set-up of the opening over-pressure. This regulation is carried out with a second wheel 28 in a manner analogous to that for the fresh gas flow.

Thus, the above description with regard to the first wheel 26 applies equally to the second wheel 28.

Oxygen flushing of the tubing system may be executed by means of a first push-button 30. This assumes that the anaesthetic device has a system for oxygen flushing that is electronically operable (an on/off operation is sufficient).

A second push-button 32 has the function of switching off alarms.

The push-buttons 30, 32 may be replaced with push functionality for the first wheel 26 and the second wheel 28 respectively.

The remote control 22 may be attached to a suitable location for the operator during manual ventilation using a hook-and-loop (Velcro®) strip 34 or some other known fastener.

It is an advantage for the remote control 22 to be provided with a sound generator 36. Sound information may improve safety while using the remote control 22. For example, the setting of values using the first 26 and the second 28 wheels is made easier if a sound is generated simultaneously with their use. One range of tones can represent an increase of a value and another range a decrease. Varying tones may also be employed. One of the parametric values, for example the flow, can be represented by a single tone and the other value (pressure) by a double tone. Alarms can be restricted to the sound generator 36, which means that a lower volume can be employed.

Another advantage of the sound generator 36 is that it can make the remote control 22 easier to find if it produces a "beep" in response to a "seek" signal from the user interface 14. The remote control 22 may also generate a "separation" alarm if the remote control 22 is out of wireless communication range with the rest of the anaesthetic device. This prevents someone taking the remote control 22 away by mistake. The remote control 22 and the user interface 14 can also carry out an identification connection between themselves.

The remote control 22 may be provided with a rechargeable battery supply. A specific holder for the remote control 22 on the anaesthetic device may be used to charge the battery when the remote control 22 is not in use. Charging may be done in a known manner, for example using a contact or inductively.

Variations in the detail of the remote control 22 may be made without departing from the invention.

For example the wheels 26, 28 need not be provided with distinct positions. They may be connected through software with the ordinary controls on the anaesthetic device so that values are changed in the same way regardless of whether the wheels or the controls on the device that are used.

Although further modifications and changes may be suggested by those skilled in the art, it is the intention of the inventor to embody within the patent warranted hereon all changes and modifications as reasonably and properly come within the scope of his contribution to the art.

We claim as our invention:

1. An anaesthesia apparatus comprising:
   a tubing system adapted for connection to a patient;
   a manual ventilation bag in communication with said tubing system;
   a mechanical ventilator in communication with said tubing system;
   a user interface allowing selected setting of an operating mode including a mechanical ventilation mode using said mechanical ventilator and a manual ventilation mode using said manual ventilation bag, and allowing parameter values to be set for the selected operating mode; and a remote control, separate from and in wireless communication with said user interface, for wirelessly transmitting commands to said user interface, said user interface responding to and implementing said commands only if said manual ventilation mode has been selected, said remote control comprising manually-actuatable controls for controlling at least one parameter selected from the group consisting of fresh gas flow, oxygen flushing, permitted over-pressure level, and alarm switch-off.

2. An anaesthesia apparatus as claimed in claim 1 wherein at least one of said controls is a rotatable wheel for regulating at least one of fresh gas flow and permitting over-pressure level.

3. An anaesthesia apparatus as claimed in claim 2 wherein said wheel has a distinct position related to a predetermined setting.

4. An anaesthesia apparatus as claimed in claim 1 wherein said remote control comprises a manually-actuable push button for regulating a parameter selected from the group consisting of oxygen flushing and alarm switch-off.

5. An anaesthesia apparatus as claimed in claim 1 wherein said remote control has a fastening device allowing fastening of said remote control to a selected location.

6. An anaesthesia apparatus as claimed in claim 1 wherein said remote control comprises a sound generator for emitting acoustic signals.

7. An anaesthesia apparatus as claimed in claim 6 wherein said remote control wirelessly receives signals transmitted from said user interface, and wherein said sound generator is operable in response to one of said signals from said user interface.

8. An anaesthesia apparatus as claimed in claim 6 wherein said sound generator emits a sound signal if said remote control is moved out of a range of wireless communication with said user interface.

* * * * *